(12) United States Patent
Marsden et al.

(10) Patent No.: US 7,341,700 B2
(45) Date of Patent: *Mar. 11, 2008

(54) METHOD FOR RECOVERY OF METALS FROM METAL-CONTAINING MATERIALS USING MEDIUM TEMPERATURE PRESSURE LEACHING

(75) Inventors: John O. Marsden, Phoenix, AZ (US); Robert E. Brewer, Safford, AZ (US); Joanna M. Robertson, Thatcher, AZ (US); Wayne W. Hazen, Lakewood, CO (US); Philip Thompson, West Valley City, UT (US); David R. Baughman, Golden, CO (US); Roland Schmidt, Golden, CO (US)

(73) Assignee: Phelps Dodge Corporation, Phoenix, AZ (US)

( * ) Notice: Subject to any disclaimer, the term of this patent is extended or adjusted under 35 U.S.C. 154(b) by 461 days.

This patent is subject to a terminal disclaimer.

(21) Appl. No.: 10/756,574

(22) Filed: Jan. 12, 2004

(65) Prior Publication Data

US 2004/0146438 A1 Jul. 29, 2004

Related U.S. Application Data

(63) Continuation of application No. 09/915,105, filed on Jul. 25, 2001, now Pat. No. 6,676,909.

(60) Provisional application No. 60/220,673, filed on Jul. 25, 2000.

(51) Int. Cl.
*C22B 15/00* (2006.01)

(52) U.S. Cl. .................. 423/28; 423/20; 423/21.1; 423/22; 423/49; 423/53; 423/109; 423/150.1; 241/23; 75/743; 75/744

(58) Field of Classification Search .................. 423/28, 423/21.5, 22, 49, 53, 20, 109, 150.1, DIG. 15, 423/21.1; 241/23; 75/743, 744
See application file for complete search history.

(56) References Cited

U.S. PATENT DOCUMENTS

| | | | |
|---|---|---|---|
| 3,260,593 A | 7/1966 | Zimmerley et al. | |
| 3,528,784 A | 9/1970 | Green | |
| 3,656,888 A | 4/1972 | Barry et al. | |
| 3,669,651 A | 6/1972 | Spedden et al. | |
| 3,673,371 A | 6/1972 | Smith et al. | |
| 3,775,099 A | 11/1973 | Coffield et al. | |
| 3,868,440 A | 2/1975 | Lindblad et al. | |
| 3,896,208 A | 7/1975 | Dubeck et al. | |
| 3,949,051 A | 4/1976 | Pawlek et al. | |
| 3,958,985 A | 5/1976 | Anderson | |
| 3,961,028 A | 6/1976 | Parker et al. | |
| 3,962,402 A | 6/1976 | Touro | |
| 3,967,958 A | 7/1976 | Coffield et al. | |
| 3,985,553 A | 10/1976 | Kunda et al. | |
| 3,991,159 A | 11/1976 | Queneau et al. | |
| 4,017,309 A | 4/1977 | Johnson | |
| 4,020,106 A | 4/1977 | Ackerley et al. | |
| 4,028,462 A | 6/1977 | Domic et al. | |
| 4,029,733 A | 6/1977 | Faugeras et al. | |
| 4,039,405 A | 8/1977 | Wong | |
| 4,039,406 A | 8/1977 | Stanley et al. | |
| 4,046,851 A | 9/1977 | Subramanian et al. | |
| 4,069,119 A | 1/1978 | Wong | |
| 4,091,070 A | 5/1978 | Riggs et al. | |
| 4,120,935 A | 10/1978 | Fountain et al. | |
| 4,150,976 A | 4/1979 | Dain | |
| 4,157,912 A | 6/1979 | Weir et al. | |
| 4,165,362 A | 8/1979 | Reynolds | |
| 4,256,553 A | 3/1981 | Baczek et al. | |
| 4,266,972 A | 5/1981 | Redondo-Abad et al. | |
| 4,272,341 A | 6/1981 | Lamb | |
| 4,338,168 A | 7/1982 | Stanley et al. | |
| 4,405,569 A | 9/1983 | Dienstbach | |
| 4,415,540 A | 11/1983 | Wilkomirsky et al. | |
| 4,442,072 A | 4/1984 | Baglin et al. | |
| 4,507,268 A | 3/1985 | Kordosky et al. | |
| 4,571,264 A | 2/1986 | Weir et al. | |
| 4,619,814 A | 10/1986 | Salter et al. | |
| 4,775,413 A | 10/1988 | Horton et al. | |

(Continued)

FOREIGN PATENT DOCUMENTS

| | | |
|---|---|---|
| AU | 0219785 | 12/1958 |
| CL | 1657-2000 | 6/1999 |
| WO | WO 01/08890 | 4/2001 |

OTHER PUBLICATIONS

Evans, et al., "International Symposium of Hydrometallurgy," Mar. 1, 1973, 2 pages.

(Continued)

*Primary Examiner*—Steven Bos
(74) *Attorney, Agent, or Firm*—Snell & Wilmer L.L.P.

(57) ABSTRACT

The present invention relates generally to a process for recovering copper and other metal values from metal-containing materials using controlled, super-fine grinding and medium temperature pressure leaching. Processes embodying aspects of the present invention may be beneficial for recovering a variety of metals such as copper, gold, silver, nickel, cobalt, molybdenum, rhenium, zinc, uranium, and platinum group metals, from metal-bearing materials, and find particular utility in connection with the extraction of copper from copper sulfide ores and concentrates.

15 Claims, 2 Drawing Sheets

U.S. PATENT DOCUMENTS

| | | |
|---|---|---|
| 4,814,007 A | 3/1989 | Lin et al. |
| 4,875,935 A | 10/1989 | Gross et al. |
| 4,880,607 A | 11/1989 | Horton et al. |
| 4,892,715 A | 1/1990 | Horton |
| 4,895,597 A | 1/1990 | Lin et al. |
| 4,971,662 A | 11/1990 | Sawyer et al. |
| 4,992,200 A | 2/1991 | Lin et al. |
| 5,028,259 A | 7/1991 | Lin et al. |
| 5,059,403 A | 10/1991 | Chen |
| 5,073,354 A | 12/1991 | Fuller et al. |
| 5,176,802 A | 1/1993 | Duyvesteyn et al. |
| 5,223,024 A | 6/1993 | Jones |
| 5,232,491 A * | 8/1993 | Corrans et al. ............... 75/743 |
| 5,316,567 A | 5/1994 | Jones |
| 5,356,457 A | 10/1994 | Alvarez et al. |
| 5,431,717 A | 7/1995 | Kohr |
| 5,573,575 A | 11/1996 | Kohr |
| 5,645,708 A | 7/1997 | Jones |
| 5,650,057 A | 7/1997 | Jones |
| 5,670,035 A | 9/1997 | Virnig et al. |
| 5,676,733 A | 10/1997 | Kohr |
| 5,698,170 A | 12/1997 | King |
| 5,730,776 A | 3/1998 | Collins et al. |
| 5,770,170 A | 6/1998 | Collins et al. |
| 5,849,172 A | 12/1998 | Allen et al. |
| 5,869,012 A | 2/1999 | Jones |
| 5,874,055 A | 2/1999 | Jones |
| 5,895,633 A | 4/1999 | King |
| 5,902,474 A | 5/1999 | Jones |
| 5,914,441 A | 6/1999 | Hunter et al. |
| 5,917,116 A | 6/1999 | Johnson et al. |
| 5,985,221 A | 11/1999 | Knecht |
| 5,989,311 A | 11/1999 | Han et al. |
| 5,993,635 A | 11/1999 | Hourn et al. |
| 6,083,730 A | 7/2000 | Kohr |
| 6,146,444 A | 11/2000 | Kohr |
| 6,149,883 A | 11/2000 | Ketcham et al. |
| 6,428,604 B1 * | 8/2002 | Kerfoot et al. ............... 75/743 |
| 6,676,909 B2 * | 1/2004 | Marsden et al. ............. 423/28 |

OTHER PUBLICATIONS

Duyesteyn, it al., "The Escondida Process for Copper Concentrates," 1998.

King, et al., "The Total Pressure Oxidation of Copper Concentrates," 1993.

King, J. A., "Autoclaving of Copper Concentrates," paper from COPPER 95, vol. III: Electrorefining and Hydrometallurgy of Copper, International Conference held in Santiago, Chile, Nov. 1995.

Mackis, V. N., "Direct Acid Pressure Leaching of Chalcocite Concentrate," vol. 19, No. 2, Feb. 1967.

Hirsch, H. E., "Leaching of Metal Sulphides," Patents, UK, No. 1,598,454, 1981, 7 pages.

Chimeilewski, T., "Pressure Leaching of a Sulphide Copper Concentrate with Simultaneous Regeneration of the Leaching Agent," Hydrometallurgy, vol. 13, No. 1, 1984, pp. 63-72.

Dannenberg, R. O., "Recovery of Cobalt and Copper from Complex Sulfide Concentrates," Government Report, 20 pages, Report No. BM RI9138, U.S. Dept. of the Interior, 1987.

Berezowsky, R.M.G.S., "The Commercial Status of Pressure Leaching Technology," JOM, vol. 43, No. 2, 1991, pp. 9-15.

Hackl, R. P., "Effect of Sulfur-Dispersing Surfactants on the Oxygen Pressure Leaching of Chalcopyrite," paper from COPPER 95, vol. III, pp. 559-577, Met Soc of CIM, Nov. 1995.

Hackl, R. P., "Passivation of Chalcopyrite During Oxidative Leaching in Sulfate Media," Hydrometallurgy, vol. 39, 1995, pp. 25-48.

L.W. Beckstead, et al., "Acid Ferric Sulfate Leaching of Attritor-Ground Chalcopyrite Concentrate," vol. II, Extractive Metallurgy of Copper, Chapter 31, pp. 611-632, no date.

Jim A. King, et al., paper entitled: "The Total Pressure Oxidation of Copper Concentrates," vol. 1, Fundamental Aspects, 1993.

Dreisinger, D. B., "Total Pressure Oxidation of El Indio Ore and Concentrate," COPPER 1999, Fourth International Conference, Phoenix, Arizona, USA, Oct. 1999.

Richmond, G. D., "The Commissioning and Operation of a Copper Sulphide Pressure Oxidation Leach Process at Mt. Grodon," ALTA COPPER 1999: Copper Sulphides Symposium & Copper Hydrometallurgy Fjorum, Gold Coast, Queensland, Australia Conference, 1999.

* cited by examiner

METHOD FOR RECOVERY OF METALS FROM METAL-CONTAINING MATERIALS USING MEDIUM TEMPERATURE PRESSURE LEACHING

CROSS-REFERENCE TO RELATED APPLICATIONS

This application is a continuation of U.S. patent application, Ser. No. 09/915,105, entitled "Method for Recovery of Metals from Metal-Containing Materials Using Medium Temperature Pressure Leaching," filed Jul. 25, 2001, now U.S. Patent 6,676,909, which claims priority to U.S. Provisional Patent Application, Ser. No. 60/220,673 entitled "Methods for Recovering Copper and Other Metals from Sulfide Concentrates Using Medium Temperature Pressure Oxidation," filed on Jul. 25, 2000, both of which are incorporated by reference herein.

FIELD OF INVENTION

The present invention relates generally to a process for recovering copper and other metal values from metal-containing materials, and more specifically, to a process for recovering copper and other metal values from metal-containing materials using controlled, super-fine grinding and medium temperature pressure leaching.

BACKGROUND OF THE INVENTION

Smelting is a well-established approach for recovering a metal, such as copper, from a metal-bearing sulfide material. Due to the high cost of smelting, however, the copper sulfide minerals in an ore body typically are first concentrated by flotation techniques to provide a smaller volume for smelting. The concentrate is then shipped to a smelter, which processes the concentrate pyrometallurgically at high temperatures to form a crude copper product that is subsequently refined to a highly pure metal.

The recovery of copper from copper sulfide concentrates using pressure leaching has proven to be a potentially economically attractive alternative to smelting. Pressure leaching operations generally produce less fugitive emissions than smelting operations, and thus, environmental benefits may be realized. Further, pressure leaching circuits may be more cost-effectively constructed on-site at a concentrator, eliminating the expense associated with concentrate transportation that smelting operations may require. Further, any byproduct acid produced in the pressure leaching circuit may be used in adjacent heap leaching operations, thus offsetting some of the costs associated with purchased acid.

The mechanism by which pressure leaching processes effectuate the release of copper from sulfide mineral matrices, such as chalcopyrite, is generally dependent on temperature, oxygen availability, and process chemistry. For example, in high temperature pressure leaching processes for chalcopyrite, that is, pressure leaching processes operating above about 200° C., it has generally been found that sulfur is fully converted to sulfate. In low temperature pressure leaching processes (i.e., below about 100° C.), it has generally been found that the chalcopyrite leaches slowly and incompletely. Medium temperature pressure leaching processes for chalcopyrite, which are generally thought of as those processes operating at temperatures from about 120° C. to about 190° C., have been the focus of much research and development in recent years and have shown some promise for achieving a satisfactory compromise between the high temperature and low temperature processes. As discussed in further detail hereinbelow, however, even with these efforts, such processes still exhibit significant processing disadvantages.

Low temperature pressure leaching processes historically have been disfavored because of characteristically low extraction of copper and other metals, and long residence times. High temperature pressure leaching processes, notwithstanding their relatively short residence times and high metal extractions, tend to have higher oxygen consumption, higher by-product acid production, and greater heat production in the pressure leaching vessel, which requires increased cooling. Prior medium temperature pressure leaching processes typically suffer incomplete copper extraction resulting from either passivation of the copper sulfide particle surfaces by a metal-polysulfide layer or partially-reacted copper sulfide particles becoming coated with liquid elemental sulfur and/or other reaction products. Further, in prior medium temperature processes, under certain conditions, molten elemental sulfur commonly agglomerates in the pressure leaching vessel to form coarse sulfur "prills" or "balls," which inhibit the extraction of copper and other metals and which can create substantial difficulties with materials handling and transport.

A variety of previous attempts have been made to circumvent the problems associated with medium temperature pressure leaching and to realize the potential benefits pursuant thereto. For example, applying known pressure leaching processes to the treatment of zinc sulfide materials, previous attempts have been made to use surfactants such as lignin derivatives, tannin compounds (such as quebracho), and orthophenylene diamine (OPD) to disperse the elemental sulfur formed and to render the copper in chalcopyrite concentrates extractable. However, these attempts have not been entirely successful since relatively low copper extraction was realized even after significant residence times.

Other attempts have included pressure oxidation in the presence of an acidic halide solution (U.S. Pat. No. 5,874,055), and the use of finely divided particulate carbonaceous material to inhibit passivation of incompletely leached copper sulfide particles (U.S. Pat. No. 5,730,776). The feasibility of using molten sulfur-dispersing surfactants to enhance pressure leaching of chalcopyrite in the temperature range of 125° C. to 155° C. has been investigated; however, it was found that chalcopyrite particles (P90 of 25-38 microns) leached too slowly even if molten sulfur was prevented from passivating the material surfaces. See Hackl et al., "Effect of sulfur-dispersing surfactants on the oxidation pressure leaching of chalcopyrite," proceedings of COPPER 95-COBRE 95 International Conference, Volume III, Electrorefining and Hydrometallurgy of Copper, The Metallurgical Society of CIM, Montreal, Canada. The authors of that study ultimately reported that the reaction rate for chalcopyrite was controlled, at least in part, by a passivating mechanism unrelated to sulfur formation.

It is generally known that hydrometallurgical processes, particularly pressure leaching processes, are sensitive to particle size. Thus, it is common practice in the area of extractive hydrometallurgy to finely divide, grind, and/or mill mineral species to reduce particle sizes prior to processing by pressure leaching. For example, U.S. Pat. No. 5,232,491 to Corrans, et al., entitled "Activation of a Mineral Species," teaches a method of activating a mineral species for oxidative hydrometallurgy by milling the species to P80 of about 30 microns or less. Further, International Publication No. WO 01/00890 to Anglo American PLC, entitled "Process for the Extraction of Copper," discusses pressure leaching of copper sulfide particles (P80 from 5-20 microns) in the presence of a surfactant material at temperatures from 130° C. to 160° C. According to test data set forth in this publication, pressure leaching of chalcopyrite under these conditions resulted in somewhat favorable copper extractions ranging from about 88.2 to about 97.9%.

It generally has been appreciated that reducing the particle size of a mineral species, such as, for example, copper sulfide, enables pressure leaching under less extreme conditions of pressure and temperature. The present inventors have observed, however, that in addition to being sensitive to the overall particle size distribution of the mineral species being processed, pressure leaching processes—namely, copper extraction by medium temperature pressure leaching processes—are sensitive to the coarsest particle sizes in the process stream above about 25 microns. Indeed, photomicrographs of autoclave residue from coarse-ground (i.e., P80 of about 30-100 microns) chalcopyrite feed material have indicated that unreacted chalcopyrite particles coarser than about 20 microns were encapsulated in elemental sulfur. It was observed that very few chalcopyrite particles finer than about 10 microns remained in the residue.

An effective and efficient method to recover copper from copper-containing materials, especially copper from copper sulfides such as chalcopyrite and chalcocite, that enables high copper recovery ratios at a reduced cost over conventional processing techniques would be advantageous.

SUMMARY OF THE INVENTION

While the way in which the present invention addresses the deficiencies and disadvantages of the prior art is described in greater detail hereinbelow, in general, according to various aspects of the present invention, a process for recovering copper and other metal values from a metal-bearing material includes various physical conditioning, reactive, and recovery processes. In particular, controlled, super-fine grinding of the metal-bearing material prior to reactive processing enhances the recovery of copper and/or other desired metal values. In accordance with the various embodiments of the present invention, controlled, super-fine grinding of the metal-bearing material prior to processing by medium temperature pressure leaching results in enhanced metal value recovery and various other advantages over prior art metal recovery processes.

In accordance with an exemplary embodiment of the present invention, a process for recovering copper from a copper-containing material generally includes the steps of: (i) providing a feed stream containing copper-containing material; (ii) subjecting the copper-containing feed stream to a controlled, super-fine grinding process; (iii) pressure leaching the copper-containing feed stream to yield a copper-containing solution; and (iv) recovering cathode copper from the copper-containing solution. As used herein, the term "pressure leaching" shall refer to a metal recovery process in which material is contacted with an acidic solution and oxygen under conditions of elevated temperature and pressure. In one aspect of a preferred embodiment of the invention, copper recovery of 98 percent is achievable while still realizing various important economic benefits. In another aspect of a preferred embodiment of the invention, the use of a dispersing agent during pressure leaching decreases undesirable agglomeration of elemental sulfur in the pressure leaching vessel and passivation of unreacted copper-bearing material particles by liquid elemental sulfur. Moreover, in another aspect of a preferred embodiment of the invention, the consumption of acid is reduced, resulting in a lower make-up acid requirement.

These and other advantages of a process according to various aspects of the present invention will be apparent to those skilled in the art upon reading and understanding the following detailed description with reference to the accompanying figures.

BRIEF DESCRIPTION OF THE DRAWINGS

The subject matter of the present invention is particularly pointed out and distinctly claimed in the concluding portion of the specification. A more complete understanding of the present invention, however, may best be obtained by referring to the detailed description and claims when considered in connection with the drawing figures, wherein like numerals denote like elements and wherein:

DETAILED DESCRIPTION

The present invention exhibits significant advancements over prior art processes, particularly with regard to recovery ratios and process efficiency. Moreover, existing copper recovery processes that utilize a conventional atmospheric or pressure leaching/solvent extraction/electrowinning process sequence may, in many instances, be easily retrofitted to exploit the many commercial benefits the present invention provides.

Figure 1:
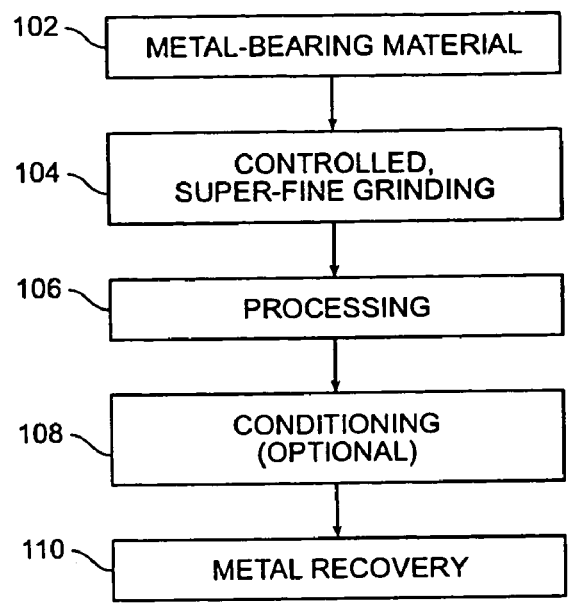
FIG. 1 illustrates a flow diagram of a copper recovery process in accordance with the present invention.

Referring to FIG. 1, in accordance with various aspects of the present invention, a metal-bearing material 102 is provided for processing. Metal-bearing material 102 may be an ore, a concentrate, or any other material from which copper and/or other metal values may be recovered. Metal values such as, for example, copper, gold, silver, zinc, platinum group metals, nickel, cobalt, molybdenum, rhenium, uranium, rare earth metals, and the like, may be recovered from metal-bearing materials in accordance with various embodiments of the present invention. The various aspects and embodiments of the present invention, however, prove especially advantageous in connection with the recovery of copper from copper sulfide ores, such as, for example, ores and/or concentrates containing chalcopyrite ($CuFeS_2$), chalcocite ($Cu_2S$), bornite ($Cu_5FeS_4$), and covellite ($CuS$), and mixtures thereof. Thus, metal-bearing material 102 preferably is a copper ore or concentrate, and most preferably, is a copper sulfide ore or concentrate.

Metal-bearing material 102 may be prepared for metal recovery processing in any manner that enables the conditions of metal-bearing material 102—such as, for example, composition and component concentration—to be suitable for the chosen processing method, as such conditions may affect the overall effectiveness and efficiency of processing operations. Desired composition and component concentration parameters can be achieved through a variety of chemical and/or physical processing stages, the choice of which will depend upon the operating parameters of the chosen processing scheme, equipment cost and material specifications. For example, as discussed in some detail hereinbelow, metal-bearing material 102 may undergo comminution, flotation, blending, and/or slurry formation, as well as chemical and/or physical conditioning before and/or after the controlled, super-fine grinding stage.

In accordance with one aspect of the present invention, metal-bearing material 102 is prepared for metal recovery processing by controlled, super-fine grinding. Preferably, a uniform, ultra-fine particle size distribution is achieved, as experimental results suggest that copper extraction by medium temperature pressure leaching is sensitive to the coarsest sizes of copper-containing material particles in the process stream. As discussed above, photomicrographs of medium temperature pressure leaching residue from coarse-ground chalcopyrite feed material (i.e., feed material not subjected to controlled, super-fine grinding in accordance with the present invention) have indicated that unreacted chalcopyrite particles coarser than about 20 microns were encapsulated in elemental sulfur. It was, however, observed that very few chalcopyrite particles finer than about 10 microns remained in the residue. The present inventors have achieved advancement in the art of copper hydrometallurgy by recognizing that it is advantageous not only to reduce the size of the copper-containing material particles in the process stream, but also to ensure that the size and weight proportion of the coarsest particles is minimized. Thus, while the prior art generally teaches finely dividing, grinding, and/or milling mineral species prior to extractive hydrometallurgical processing such that, for example, approximately 80 percent of the particles are less than a certain size (e.g., P80 of less than about 20 microns, see International Publication No. WO 01/0890; P80 of less than about 30 microns, see U.S. Pat. No. 5,232,491; etc.), the prior art generally allows a significant fraction (e.g., at least 20 percent) of the particles in the process stream to be larger than about 20 microns. As mentioned above, particles coarser than about 20 microns have been shown not to react completely during medium temperature leaching, but are occluded from reaction by elemental sulfur and/or other byproducts. Significant advantages in processing efficiency and copper recovery ratios are achievable by enabling substantially all particles to react substantially completely. For example, P80 distributions and other similar manners of expressing size distributions do not generally enable such results.

As used herein, the term "controlled, super-fine grinding" refers to any process by which the particle size of the material being processed is reduced such that substantially all of the particles are small enough to react substantially completely during medium temperature pressure leaching. For example, in accordance with one aspect of the present invention, a particle size distribution of approximately 98 percent passing about 25 microns is preferable, and more preferably, the copper-containing material stream has a particle size distribution of approximately 98 percent passing from about 10 to about 23 microns, and optimally from about 13 to about 15 microns. These particle size distributions were determined through the use of a Malvern optical particle size analyzer. Other methods and apparatus, however, may be utilized.

In accordance with one aspect of an exemplary embodiment of the invention, satisfactory controlled, super-fine grinding of chalcopyrite concentrate with an as-received particle size of approximately 98 percent passing about 172 microns may be achieved using an Isamill ultra-fine grinding apparatus, a stirred horizontal shaft ball mill with baffles developed jointly by Mount Is a Mines (MIM), Australia, and Netzsch Feinmahltechnik, Germany. Preferably, if an Isamill is utilized, the grinding media used is 1.2/2.4 mm or 2.4/4.8 mm Colorado sand, available from Oglebay Norton Industrial Sands Inc., Colorado Springs, Colo. This silica sand exhibits desirable characteristics such as roundness and sphericity. However, any grinding medium that enables the desired particle size distribution to be achieved may be used, the type and size of which may be dependent upon the application chosen, the product size desired, grinding apparatus manufacturer's specifications, and the like. Exemplary media include sand, silica, metal beads, ceramic beads, and ceramic balls.

Preferably, grinding in accordance with the present invention proceeds in a staged or closed-circuit manner. That is, preferably the coarsest particles of metal-bearing material 102 are suitably ground to the desired level, while particles already at or below the desired level are not subjected to additional grinding. As such, cost savings can be obtained in connection with grinding operations, while at the same time limiting the size and weight proportion of the coarsest particles.

Referring again to FIG. 1, after metal-bearing material 102 has been suitably prepared for processing by controlled, super-fine grinding 104 and, optionally, other physical and/or chemical conditioning processes, it is subjected to a reactive processing step 106, for example, metal extraction. However, reactive processing step 106 may be any suitable process or reaction that puts the copper in metal-bearing material 102 in a condition such that it may be subjected to later copper recovery processing. In accordance with one embodiment of the present invention, reactive processing step 106 comprises medium temperature pressure leaching. Preferably, reactive processing step 106 is a medium temperature pressure leaching process operating at a temperature in the range of about 140° C. to about 180° C. and more preferably in the range of about 150° C. to about 175° C. Generally, the present inventors have found that temperatures above about 160° C., and more preferably in the range of about 160° C. or about 165° C. to about 175° C. are useful in connection with the various aspects of the present invention.

In accordance with a particularly preferred aspect of the present invention, the optimum temperature range selected for operation will tend to maximize the extraction of copper and other metals, minimize acid consumption, and thereby minimize make-up acid requirements. That is, at higher temperatures, sulfide sulfur generally is converted to sulfate according to the following reaction:

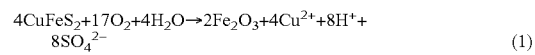

$$4CuFeS_2+17O_2+4H_2O \rightarrow 2Fe_2O_3+4Cu^{2+}+8H^++8SO_4^{2-} \qquad (1)$$

However, at high acid levels, copper extraction is lowered, likely due to the wetting characteristics of the elemental sulfur. At lower temperatures, acid is generally consumed and elemental sulfur is formed according to the following reaction:

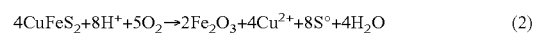

$$4CuFeS_2+8H^++5O_2 \rightarrow 2Fe_2O_3+4Cu^{2+}+8S°+4H_2O \qquad (2)$$

Preferably, in accordance with the present invention, the temperature is suitably selected to achieve an advantageous balance between reactions (1) and (2), but tending to reduce acid consumption and thus the costs associated with acid make-up, but without sacrificing copper extraction.

Reactive processing step 106 may occur in any pressure leaching vessel suitably designed to contain the pressure leaching mixture at the desired temperature and pressure conditions for the requisite pressure leaching residence time. In accordance with one aspect of a preferred embodiment of the invention, the pressure leaching vessel used in processing step 106 is an agitated, multi-compartment pressure leaching vessel. However, it should be appreciated that any pressure leaching vessel that suitably permits metal-bearing material 102 to be prepared for copper recovery may be utilized within the scope of the present invention.

During reactive processing step 106, copper and/or other metal values may be solubilized or otherwise liberated in preparation for later recovery processes. Any substance that assists in solubilizing the metal value, and thus releasing the metal value from a metal-bearing material, may be used. For example, where copper is the metal being recovered, an acid, such as sulfuric acid, may be contacted with the copper-bearing material such that the copper may be solubilized for later recovery steps. However, it should be appreciated that any suitable method of solubilizing metal values in preparation for later metal recovery steps may be utilized within the scope of this invention.

Subsequent to metal-bearing material 102 undergoing reactive processing step 106, the copper and/or other metal values that have been made available by the reactive process undergo one or more of various metal recovery processes. Referring again to FIG. 1, metal recovery process 110 may be any process for recovering copper and/or other metal values, and may include any number of preparatory or conditioning steps (optional step 108). For example, a copper-bearing solution may be prepared and conditioned for metal recovery through one or more chemical and/or physical processing steps. The product stream from reactive processing step 106 may be conditioned to adjust the composition, component concentrations, solids content, volume, temperature, pressure, and/or other physical and/or chemical parameters to desired values and thus to form a suitable copper-bearing solution. Generally, a properly conditioned copper-bearing solution will contain a relatively high concentration of soluble copper, for example, copper sulfate, in an acid solution and preferably will contain few impurities. Moreover, the conditions of the copper-bearing solution preferably are kept substantially constant to enhance the quality and uniformity of the copper product ultimately recovered.

In one aspect of a preferred embodiment of the present invention, conditioning of a copper-containing solution for copper recovery in an electrowinning circuit begins by adjusting certain physical parameters of the product slurry from the reactive processing step. In a preferred aspect of this embodiment of the invention, wherein the reactive processing step is medium temperature pressure leaching, it is desirable to reduce the temperature and pressure of the product slurry to approximately ambient conditions. A preferred method of so adjusting the temperature and pressure characteristics of the copper-containing product slurry from a medium temperature pressure leaching stage is atmospheric flashing. Further, flashed gases, solids, solutions, and steam may optionally be suitably treated, for example, by use of a venturi scrubber wherein water may be recovered and hazardous materials may be prevented from entering the environment. In accordance with further aspects of this preferred embodiment, after the product slurry has been subjected to atmospheric flashing using, for example, a flash tank, to achieve approximately ambient conditions of pressure and temperature, the product slurry may be further conditioned in preparation for later metal-value recovery steps. For example, one or more solid-liquid phase separation stages may be used to separate solubilized metal solution from solid particles. This may be accomplished in any conventional manner, including use of filtration systems, counter-current decantation (CCD) circuits, thickeners, and the like. A variety of factors, such as the process material balance, environmental regulations, residue composition, economic considerations, and the like, may affect the decision whether to employ a CCD circuit, a thickener, a filter, or any other suitable device in a solid-liquid separation apparatus. However, it should be appreciated that any technique of conditioning the product slurry for later metal value recovery is within the scope of the present invention.

As further discussed hereinbelow, the separated solids may further be subjected to later processing steps, including precious metal or other metal value recovery, such as, for example, recovery of gold, silver, platinum group metals, molybdenum, zinc, nickel, cobalt, uranium, rhenium, rare earth metals, and the like, by cyanidation or other techniques. Alternatively, the separated solids may be subject to impoundment or disposal.

The liquid separated from a solid-liquid separation apparatus also may undergo a series of conditioning steps to prepare the copper solubilized therein for recovery. For example, the separated liquid may undergo various reagent additions and/or solvent extraction stages to put the copper in a state such that the copper is susceptible to conventional copper recovery techniques. Further, subsequent conditioning and/or processing steps may be undertaken such that recovery rates are as efficient as possible.

After any desired preparation steps, the pressure leaching product stream undergoes the desired copper recovery step. The copper recovery step may include any suitable conditioning and/or copper recovery method or methods, for example, electrowinning, precipitation, solvent extraction (sometimes referred to as solution extraction or liquid ion exchange), ion exchange, and/or ion flotation, and preferably results in a relatively pure copper product.

Figure 2:
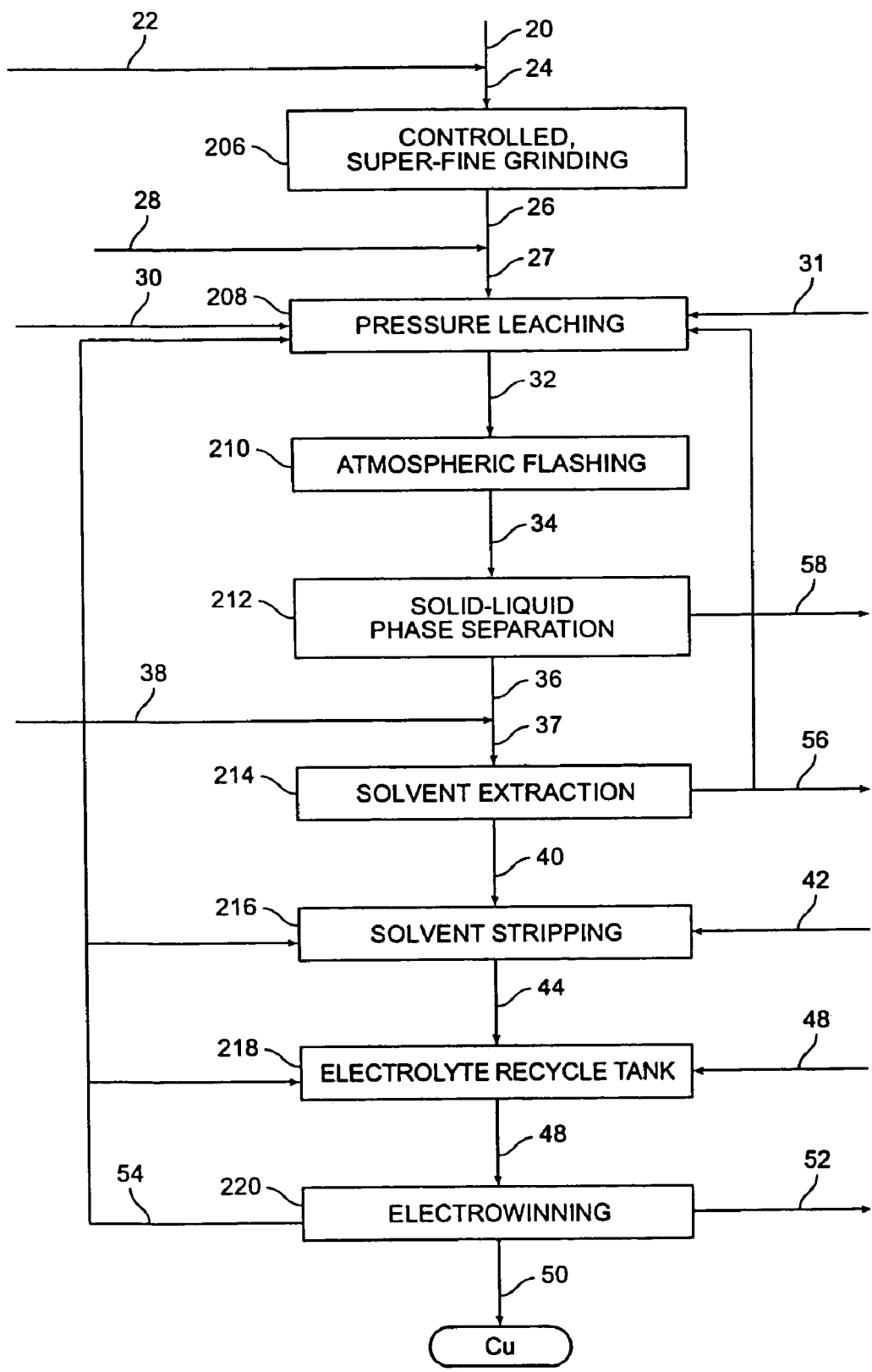
FIG. 2 illustrates a flow diagram of a copper recovery process in accordance with another embodiment of the present invention; and, FIG. 3 illustrates a graphical profile of copper extraction as a function of temperature and time in accordance with various embodiments of the present invention.

In an exemplary embodiment of the present invention illustrated in FIG. 2, a copper-containing feed stream 20 containing a copper-bearing material is provided for metal value recovery. The copper in the copper-bearing material may be in any form from which copper may be extracted, such as copper oxide or copper sulfide, for example chalcopyrite ($CuFeS_2$), chalcocite ($Cu_2S$), bornite ($Cu_5FeS_4$), and covellite (CuS). The copper-bearing material also may include any number of a variety of other metals, such as gold, silver, platinum group metals, zinc, nickel, cobalt, molybdenum, rhenium, rare earth metals, uranium, and/or mixtures thereof.

The feed stream of copper-bearing material can be provided in any number of ways, such that the conditions of the feed stream are suitable for the medium temperature pressure leaching aspect of the present invention. For example, feed stream conditions such as particle size, composition, and component concentrations can affect the overall effectiveness and efficiency of medium temperature pressure leaching.

In accordance with one aspect of the invention, the initial copper-bearing feed material may be comminuted to facilitate fluid transport and/or to optimize the inlet conditions for the controlled, super-fine grinding operation. A variety of acceptable techniques and devices for reducing the particle size of the copper-bearing material are currently available, such as ball mills, tower mills, grinding mills, attrition mills, stirred mills, horizontal mills and the like, and additional techniques may later be developed that may achieve the desired result of reducing the, particle size of the copper-bearing material to be transported.

FIG. 2 illustrates an embodiment of the present invention wherein a copper-bearing material stream 24 is a copper sulfide concentrate, such as a chalcopyrite concentrate. In one aspect of a preferred embodiment of the present invention, the copper-bearing material stream 24 is fed from a surge pile or tank (not shown) to a controlled, super-fine grinding unit 206. Process water 22 is preferably added to copper-bearing material stream 24 to bring the percent solids to the optimal pulp density specified for the controlled, super-fine grinding unit 206. In preparation for pressure leaching processing (step 208), the particle size of copper-bearing material stream 24 is reduced in a controlled, super-fine grinding unit 206. Controlled, super-fine grinding unit 206 may comprise any milling or grinding apparatus or combination of apparatus suitable to produce a fine, particle size distribution for ground copper-containing material stream 26. A variety of apparatus are available for this purpose, including, for example, ball mills, tower mills, attrition mills, stirred mills, horizontal mills, and the like, and additional techniques and apparatus may later be developed that may achieve the controlled, super-fine grinding described herein. As previously mentioned, grinding in accordance with the present invention may proceed in a staged or closed-circuit manner. That is, preferably the coarsest particles of metal-bearing material 102 are suitably ground to a desired level, while particles already at the desired level are not subjected to further grinding.

Controlled, super-fine grinding serves several functions advantageous to the hydrometallurgical processing of copper sulfides, such as chalcopyrite. First, it increases the surface area of the copper sulfide particles, thereby increasing reaction kinetics. Moreover, controlled, super-fine grinding increases the liberation of copper sulfide mineral particles from gangue and it reduces copper sulfide slurry abrasion such that the slurry may be more easily introduced to the pressure leaching unit. In accordance with one aspect of the present invention, the particle size of the copper-containing material stream is reduced by controlled, super-fine grinding to a 98 percent passing size (i.e., P98) of less than about 25 microns, and more preferably, to a P98 of from about 10 to about 23 microns, and most preferably from about 13 to about 15 microns.

In one aspect of a preferred embodiment of the present invention, the controlled, super-finely ground copper-containing material 26 is combined with a liquid 28 to form a copper-containing inlet stream 27. Preferably, the liquid comprises process water, but any suitable liquid may be employed, such as, for example, recycled raffinate, pregnant leach solution, or lean electrolyte.

The combination of liquid 28 with the controlled, super-finely ground copper-containing material 26 can be effectuated using any one or more of a variety of techniques and apparatus, such as, for example, in-line blending or using a mixing tank or other suitable vessel. In accordance with a preferred aspect of this embodiment, the material stream is concentrated with the copper-containing material being on the order less than about 50 percent by weight of the stream, and preferably about 40 percent by weight of the stream. Other concentrations that are suitable for transport and subsequent processing may, however, be used.

With continued reference to FIG. 2, inlet stream 27 is suitably introduced to a pressure leaching vessel to undergo medium temperature pressure leaching; as such, the pressure leaching vessel preferably comprises an agitated, multi-compartment pressure leaching vessel 208. As discussed in detail above, inlet stream 27 preferably has a solid particle size suitably dimensioned such that the size distribution of no more than about 2% of the concentrated copper-containing material is larger than about 23 microns (i.e., P98 of less than about 23 mm). In accordance with a preferred aspect of this embodiment, inlet stream 27 has a preferred solid-liquid ratio ranging from about 5 percent to about 50 percent solids by weight, and preferably from about 10 percent to about 35 percent solids by weight.

Any agent capable of assisting in the solubilization of the copper, such as, for example, sulfuric acid, may be provided during the pressure leaching process in a number of ways. For example, such acid may be provided in a cooling stream provided by the recycle of the raffinate solution 56 from the solvent extraction step 214 and/or by the production during pressure leaching of a sulfuric acid from the oxidation of the sulfide minerals in the feed slurry. However, it should be appreciated that any method of providing for the solubilization of copper is within the scope of the present invention. The amount of acid added during pressure leaching preferably is balanced according to the acid needed to optimize copper extraction. When optimal copper recovery is attained, the elemental sulfur formed as a reaction byproduct becomes intimately associated with the hematite byproduct as it is precipitated and generally does not significantly impact the copper leaching reaction. At high (i.e., much greater than stoichiometric) acid dosages, however, the amount of hematite precipitated in the pressure leaching vessel generally decreases and the byproduct elemental sulfur may encapsulate and/or passivate unreacted chalcopyrite particles. In addition, the sulfur may form agglomerates. The formation of these elemental sulfur agglomerates—or sulfur "prills" as they are sometimes called—is generally associated with decreased copper recovery, as discussed above.

The amount of acid introduced into medium temperature pressure leaching vessel 208 varies depending upon the reaction conditions, particularly, reaction temperature. In certain cases, make-up acid is introduced on the order of from about 300 to about 650 kilograms per tonne of concentrate, or less; however, lower make-up acid is required at higher temperatures. For example, at 160° C., copper extraction of 98.0% was achieved at a net chemical acid consumption of 320 kg/tonne. At 170° C., copper extraction of 98.0% was achieved at a net chemical acid consumption of 250 kg/tonne. At 180° C., copper extraction of 98.1% was achieved at a net chemical acid consumption of 225 kg/tonne (however, during this test, prills may have been formed and, as such, actual copper extraction may vary).

The medium temperature pressure leaching process in pressure leaching vessel 208 occurs in a manner suitably designed to promote substantially complete solubilization of the copper. Various parameters influence the medium temperature pressure leaching process. For example, during pressure leaching, it may be desirable to introduce materials to enhance the pressure leaching process. In accordance with one aspect of the present invention, during pressure leaching in pressure leaching vessel 208, sufficient oxygen 31 is injected into the vessel to maintain an oxygen partial pressure from about 50 to about 200 psi, preferably from about 75 to about 150 psi, and most preferably from about 100 to about 125 psi. Furthermore, due to the nature of medium temperature pressure leaching, the total operating pressure in pressure leaching vessel 208 is generally superatmospheric, preferably from about 100 to about 750 psi, more preferably from about 300 to about 700 psi, and most preferably from about 400 to about 600 psi.

The residence time for the medium temperature pressure leaching process can vary, depending on factors such as, for example, the characteristics of the copper-bearing material and the operating pressure and temperature of the pressure leaching vessel. In one aspect of a preferred embodiment of the invention, the residence time for the medium temperature pressure leaching of chalcopyrite ranges from about 30 to about 180 minutes, more preferably from about 60 to about 120 minutes, and most preferably on the order of about 90 minutes.

Control of the pressure leaching process, including control of the temperature in pressure leaching vessel 208, may be accomplished by any conventional or hereafter devised method. For example, with respect to temperature control, preferably the pressure leaching vessel includes a feedback temperature control feature. For example, in accordance with one aspect of the invention, the temperature of the pressure leaching vessel 208 is maintained at a temperature in the range of about 140° C. to about 180° C. and more preferably in the range of about 150° C. to about 175° C. Generally, the present inventors have found that temperatures above about 160° C., and more preferably in the range of about 160° C. or about 165° C. to about 175° C. are useful in connection with the various aspects of the present invention. Due to the exothermic nature of pressure leaching of metal sulfides, the heat generated by medium temperature pressure leaching is generally more than that needed to heat feed slurry 27 to the desired operating temperature. Thus, in order to maintain preferable pressure leaching temperature, a cooling liquid may be introduced into the pressure leaching vessel during pressure leaching. In accordance with one aspect of this embodiment of the present invention, a cooling liquid is preferably contacted with the feed stream in pressure leaching vessel 208 during pressure leaching. Cooling liquid may comprise make-up water, but can be any suitable cooling fluid from within the refining process or from an outside source, such as recycled liquid phase from the product slurry or a mixture of cooling fluids. Cooling liquid may be introduced into pressure leaching vessel 208 through the same inlet as feed slurry, or alternatively in any manner that effectuates cooling of feed slurry 27. The amount of cooling liquid added to feed slurry 27 during pressure leaching may vary according to the amount of sulfide minerals in and the pulp density of the feed slurry 27, as well as other parameters of the pressure leaching process. In a preferred aspect of this embodiment of the invention, a sufficient amount of cooling liquid is added to pressure leaching vessel 208 to yield a solids content in product slurry 32 on the order of less than about 50% solids by weight, more preferably ranging from about 3 to about 35% solids by weight, and most preferably ranging from about 8 to about 20% solids by weight.

In accordance with a preferred aspect of the present invention, medium temperature pressure leaching 208 of inlet stream 27 is performed in the presence of a dispersing agent 30. Suitable dispersing agents useful in accordance with this aspect of the present invention include, for example, organic compounds such as lignin derivatives, such as, for example, calcium and sodium lignosulfonates, tannin compounds, such as, for example, quebracho, orthophenylene diamine (OPD), alkyl sulfonates, such as, for example, sodium alkylbenzene sulfonates, and combinations of the above. Dispersing agent 30 may be any compound that resists substantial degradation in the temperature range of medium temperature pressure leaching (i.e., from about 140° C. to about 180° C.) and that achieves the desired result of preventing elemental sulfur produced during the medium temperature pressure leaching process—and thus present in the pressure leaching vessel—from agglomerating and from wetting the surface of the copper-containing material being processed. Dispersing agent 30 may be introduced to pressure leaching vessel 208 in an amount and/or at a concentration sufficient to achieve the desired result. In one aspect of a preferred embodiment of the invention, favorable results are achievable during pressure leaching of chalcopyrite using calcium lignosulfonate in an amount of about 2 to about 20 kilograms per tonne, and more preferably in an amount of about 10 kilograms per tonne of chalcopyrite concentrate.

In accordance with a preferred aspect of the embodiment of the invention illustrated in FIG. 2, product slurry 32 from pressure leaching vessel 208 may be flashed in an atmospheric flash tank 210 or other suitable vessel to release pressure and to evaporatively cool product slurry 32 through the release of steam to form a flashed product slurry 34. Depending upon the specific process equipment configurations and specifications, more than one flash stage may be employed. Flashed product slurry 34 preferably has a temperature ranging from about 90° C. to about 105° C., a copper concentration of from about 35 to about 60 grams/liter, and an acid concentration of from about 10 to about 60 grams/liter.

Referring still to FIG. 2, flashed product slurry 34 may be directed to a solid-liquid separation apparatus 212, such as a CCD circuit. Alternatively, the solid-liquid separation apparatus may comprise, for example, a thickener or a filter. In one aspect of a preferred embodiment of the invention, solid-liquid phase separation step 212 may be carried out with a conventional CCD utilizing conventional countercurrent washing of the residue stream to recover leached copper to the copper-containing solution product and to minimize the amount of soluble copper advancing to precious metal recovery processes or storage. Preferably, large wash ratios are utilized to enhance the effectiveness of the solid-liquid separation stage—that is, relatively large amounts of wash water are added to the residue stream in CCD circuit 212. Preferably, flash product slurry 34 is diluted by the wash water in CCD circuit 212 to form a copper-containing solution having a copper concentration of from about 30 to about 60 grams/liter.

Depending on its composition, residue stream 58 from solid-liquid separation apparatus 212 may be disposed of or subjected to further processing, such as, for example, precious metal recovery. For example, if residue stream 58 contains an economically significant fraction of gold, it may be desirable to recover this gold fraction through a cyanidation process or other suitable recovery process. If gold or other precious metals are to be recovered from residue stream 58 by cyanidation techniques, the content of contaminants in the stream, such as elemental sulfur, iron precipitates, and unreacted copper minerals, is preferably minimized. Such materials generally promote high reagent consumption in the cyanidation process and thus increase the expense of the precious metal recovery operation. Additionally, as mentioned above, it is preferable to use a large amount of wash water or other diluent during the solid-liquid separation process to maintain low copper and acid levels in the CCD residue in an attempt to optimize the residue stream conditions for precious metal recovery.

Referring still to FIG. 2, in accordance with various aspects of the present invention, the recovery of copper may be accomplished through conventional solvent extraction and electrowinning techniques. For example, a diluting solution 38 may be contacted with the separated liquid 36 from solid-liquid separation apparatus 212 to reduce the acid concentration of the separated liquid 36 sufficiently to provide desirable equilibrium conditions for solvent extraction 214. Solution 38 may be any suitable liquid, for example, water or atmospheric leach effluent solution, that sufficiently reduces the copper and acid concentrations to desired levels. In a preferred aspect of this embodiment of the invention, sufficient amount of solution 38 is contacted with the separated liquid stream 36 to yield an acid concentration in the diluted copper-containing solution 37 preferably ranging from about 2 to about 25 grams/liter, and more preferably from about 4 to about 7 grams/liter and a pH preferably ranging from about pH 1.5 to about pH 2.5 and more preferably from about pH 1.8 to about pH 2.2, and optimally in the range of about pH 2.0.

The diluted copper-containing solution 37 may be further processed in a solvent extraction step 214. During solvent extraction 214, copper from copper-containing solution 29 may be loaded selectively onto an organic chelating agent, for example, an aldoxime/ketoxime blend, resulting in a copper-containing organic stream 40 and a raffinate solution 56. Raffinate 56 from solvent extraction step 214 may be used beneficially in a number of ways. For example, all or a portion of raffinate 56 maybe recycled to pressure leaching vessel 10 for temperature control or may be used in heap leaching operations, or may be used for a combination thereof. The use of raffinate 56 in heap leaching operations may be beneficial because the acid and ferric iron values contained in raffinate 56 can act to optimize the potential for leaching oxide and/or sulfide ores that commonly dominate heap leaching operations. That is, the ferric and acid concentrations of raffinate 56 may be used to optimize the Eh and pH of heap leaching operations. It should be appreciated that the properties of raffinate 56, such as component concentrations, may be adjusted in accordance with the desired use of raffinate 56.

Copper-containing organic stream 40 is then subjected to a solvent stripping phase 216, wherein more acidic conditions are used to shift the equilibrium conditions to cause the copper in the reagents to be exchanged for the acid in a highly acidic stripping solution. As shown in FIG. 2, an acid-bearing reagent 42, preferably sulfuric acid, and optionally, lean electrolyte 54, are contacted with copper-containing organic stream 40 during solvent stripping phase 216. Sulfuric acid is a preferred acid-bearing reagent and is a desirable copper matrix for electrowinning operations. The acid-bearing reagent is contacted with the copper-containing organic stream to effectuate the exchange of acid for copper to provide copper for electrowinning.

Referring still to FIG. 2, copper-containing solution stream 44 from solvent stripping phase 216 may be sent to an electrolyte recycle tank 218. The electrolyte recycle tank may suitably facilitate process control for electrowinning stage 220, as will be discussed in greater detail below. Copper-containing solution stream 44, which generally contains from about 35 to about 50 grams/liter of copper and from about 145 to about 180 grams/liter acid, is preferably blended with a lean electrolyte 54 (i.e., electrolyte that has already been through the metal recovery phase and has had a portion of its dissolved copper removed) and makeup fluid 46, such as, for example, water, in the electrolyte recycle tank 218 at a ratio suitable to yield a product stream 48, the conditions of which may be chosen to optimize the resultant product of electrowinning step 220.

Preferably, the copper composition of product stream 48 is maintained substantially constant at a value from about 20 to about 60 grams/liter, more preferably at a value from about 30 to about 50 grams/liter. Copper values from the copper-containing product stream 48 are removed during electrowinning step 220 to yield a pure, cathode copper product. It should be appreciated that in accordance with the various aspects of the invention, a process wherein, upon proper conditioning of the copper-containing solution, a high quality, uniformly-plated cathode copper product may be realized without subjecting the copper-containing solution to solvent extraction prior to entering the electrowinning circuit is within the scope of the present invention. As previously noted, careful control of the conditions of the copper-containing solution entering an electrowinning circuit—especially maintenance of a substantially constant copper composition in the stream—can enhance the quality of the electrowon copper by, among other things, enabling even plating of copper on the cathode and avoidance of surface porosity in the cathode copper, which degrades the copper product and thus diminishes its economic value. In accordance with this aspect of the invention, such process control can be accomplished using any of a variety of techniques and equipment configurations, so long as the chosen system and/or method maintains a sufficiently constant feed stream to the electrowinning circuit. As those skilled in the art are aware, a variety of methods and apparatus are available for the electrowinning of copper and other metal values, any of which may be suitable for use in accordance with the present invention, provided the requisite process parameters for the chosen method or apparatus are satisfied. The Examples set forth hereinbelow are illustrative of various aspects of certain preferred embodiments of the present invention. The process conditions and parameters reflected therein are intended to exemplify various aspects of the invention, and are not intended to limit the scope of the claimed invention.

EXAMPLE 1

As discussed in detail hereinabove, controlled, super-fine grinding of chalcopyrite concentrates is preferred prior to medium temperature pressure leaching at about 140° C. to about 180° C. to prevent encapsulation of unreacted copper minerals by elemental sulfur and/or copper polysulfide. The various grinding systems set forth below were used to produce an ultra-finely ground inlet stream of chalcopyrite concentrate samples containing approximately 30.5 percent copper for a medium temperature pressure leaching pilot plant. The as-received particle size of the chalcopyrite concentrate sample used in the continuous pilot plant tests was P98=approximately 101 microns. The as-received particle size of the chalcopyrite concentrate sample used in the batch tests was P98=approximately 172 microns.

1) Conventional regrind mill followed by a short grind in a Union Process stirred pin mill—material was reground in a conventional regrind mill for sixty (60) minutes followed by five (5) minutes in a Union Process batch stirred mill.

2) Conventional regrind mill followed by a longer grind in a Union Process stirred pin mill—material was reground in a conventional regrind mill for sixty (60) minutes followed by twenty (20) minutes in a Union Process batch stirred mill.

3) Open circuit Metprotech mill—material was ground for thirty (30) minutes in a continuous Metprotech vertical stirred pin mill. Steel media (approximately 4 mm) was used.

4) Closed circuit Metprotech mill—material was ground for thirty (30) minutes in a continuous Metprotech mill, then cycloned with a 2 inch cyclone. Underflow was ground for fifteen (15) minutes in a continuous Metprotech mill and combined with the cyclone overflow as final product.

5) Single pass Netzsch mill—material was ground in a single pass using a continuous Netzsch 4 liter mill and a net energy input of 56 kWhr/tonne. Colorado sand media (1.2/2.4 mm or 2.4/4.8 mm) was used as the grinding media.

6) Double pass Netzsch mill—material was ground twice in the continuous Netzsch mill. The single pass material was ground in another pass through the mill using a net energy input of 56 kWhr/tonne for the second pass. Colorado sand media (1.2/2.4 mm) was used as the grinding media.

Continuous pilot plant results indicate that copper extraction is sensitive to grind fineness. For example, it was observed that a grind fineness of approximately 98 percent passing about 23 microns was required to achieve approximately 98 percent copper extraction at about 160° C. and about 500 kg/tonne sulfuric acid addition to the pressure leaching vessel. It was further observed that a grind fineness of approximately 98 percent passing about 12 microns was required to achieve approximately 98 percent copper extraction at about 170° C. and about 400 kg/tonne sulfuric acid addition to the pressure leaching vessel.

TABLE 1

Copper Extraction versus Grind Fineness in Continuous Pilot Plant Tests

| Grinding System | Size in Microns | | | | % Cu Extracted | Residue wt % Cu |
| --- | --- | --- | --- | --- | --- | --- |
| | $P_{80}$ | $P_{90}$ | $P_{95}$ | $P_{98}$ | | |
| 160° C., 500 kg/tonne $H_2SO_4$ | | | | | | |
| 1 | 24.6 | 34.5 | 43.4 | 52.2 | 93.0 | 2.99 |
| 3 | 6.4 | 10.8 | 18.9 | 31.3 | 97.0 | 0.92 |
| 4 | 5.5 | 8.5 | 13.7 | 23.2 | 98.3 | 0.72 |
| 2 | 6.7 | 10.2 | 17.0 | 22.3 | 98.6 | 0.67 |
| 170° C. | | | | | | |
| 5* | 7.7 | 11.7 | 16.5 | 23.9 | 96.9 | 1.39 |
| 6** | 6.2 | 7.8 | 9.2 | 12.1 | 98.1 | 0.76 |

*500 kg/tonne $H_2SO_4$
**400 kg/tonne $H_2SO_4$

EXAMPLE 2

Batch results also indicate that copper extraction is sensitive to grind fineness. The batch tests were performed to confirm that the products of Netzsch mill processing would react similarly to the products of Metprotech processing. The grinding systems indicated in Table 2 correspond to the grinding systems identified in Example 1.

TABLE 2

Copper Extraction versus Grind Fineness in Batch Tests

| Grinding System | Size in Microns | | | | % Cu Extracted | Residue wt % Cu |
| --- | --- | --- | --- | --- | --- | --- |
| | $P_{80}$ | $P_{90}$ | $P_{95}$ | $P_{98}$ | | |
| 160° C., 500 kg/tonne $H_2SO_4$ | | | | | | |
| 5 | 9.8 | 13.8 | 18.9 | 27.8 | 97.7 | 0.954 |
| 5 | 9.9 | 13.6 | 18.6 | 28.1 | 98.4 | 0.664 |
| 4 | 5.7 | 9.4 | 13.9 | 21.3 | 99.2 | 0.327 |
| 6 | 6.2 | 7.8 | 9.2 | 12.1 | 99.2 | 0.358 |
| 170° C., 500 kg/tonne $H_2SO_4$ | | | | | | |
| 5 | 9.8 | 13.8 | 18.9 | 27.8 | 95.1 | 1.930 |
| 6 | 6.2 | 7.8 | 9.2 | 12.1 | 99.2 | 0.343 |

EXAMPLE 3

Figure 3:
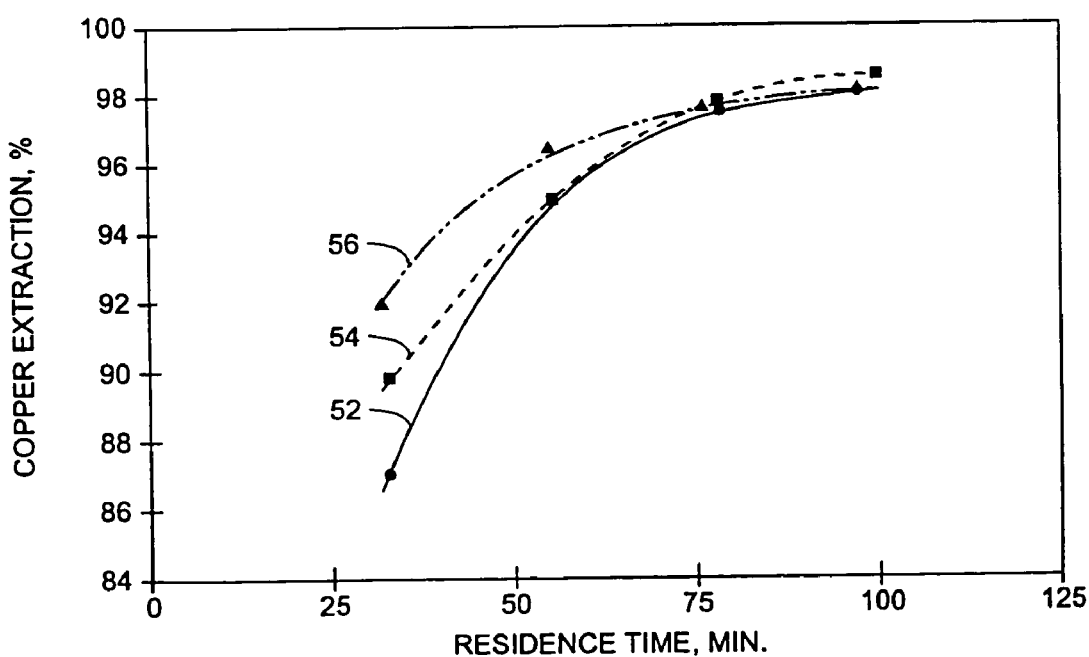

FIG. 3 is a graphical profile of continuous pilot plant test data illustrating copper extraction as a function of time in accordance with various embodiments of the present invention. For each test run, the chalcopyrite concentrate samples were ground to a P98 of less than about 23 microns. Calcium lignosulfonate from Georgia Pacific Corp. was introduced to the pressure leaching vessels in an amount of about 10 kilograms per tonne of concentrate.

Curve 52 illustrates copper extraction versus residence time for medium temperature pressure leaching of chalcopyrite at approximately 160° C., with acid addition to the pressure leaching vessel of about 580 kilograms per tonne. Approximately 96% copper extraction was achieved at about 60 minutes, and 98+% copper extraction was achieved at a residence time of about 95 minutes.

Curve 54 illustrates copper extraction versus residence time for medium temperature pressure leaching of chalcopyrite at approximately 170° C., with acid addition to the pressure leaching vessel of about 507 kilograms per tonne. Approximately 96% copper extraction was achieved at about 60 minutes, and 98+% copper extraction was achieved at a residence time of about 80 minutes.

Curve 56 illustrates copper extraction versus residence time for medium temperature pressure leaching of chalcopyrite at approximately 180° C., with acid addition to the pressure leaching vessel of about 421 kilograms per tonne. Approximately 96% copper extraction was achieved at about 52 minutes, and 98+% copper extraction was achieved at a residence time of about 90 minutes (however during this test prills may have been formed and, as such, actual copper extraction may vary).

An effective and efficient method to recover copper from copper-containing materials, especially copper from copper sulfides, such as chalcopyrite, that enables high copper recovery ratios at a reduced cost over conventional processing techniques has been presented herein. In accordance with the present invention, it has been shown that copper recovery in excess of 98 percent is achievable while realizing various important economic benefits of medium temperature pressure leaching and circumventing processing problems historically associated with medium temperature pressure leaching. The use of a dispersing agent during pressure leaching lessens undesirable agglomeration of elemental sulfur in the pressure leaching vessel and passivation of unreacted copper-bearing material particles by liquid elemental sulfur. Further, the present inventors advanced the art of copper hydrometallurgy by recognizing the advantages of not only reducing the size of the copper-containing material particles in the process stream, but also ensuring that the size and weight proportion of the coarsest particles are minimized.

The present invention has been described above with reference to a number of exemplary embodiments and examples. It should be appreciated that the particular embodiments shown and described herein are illustrative of the invention and its best mode and are not intended to limit in any way the scope of the invention as set forth in the claims. Those skilled in the art having read this disclosure will recognize that changes and modifications may be made to the exemplary embodiments without departing from the scope of the present invention. Further, although certain preferred aspects of the invention are described herein in terms of exemplary embodiments, such aspects of the invention may be achieved through any number of suitable means now known or hereafter devised. Accordingly, these and other changes or modifications are intended to be included within the scope of the present invention, as expressed in the following claims.

What is claimed is:

1. A method for recovering metal from a metal-bearing material, comprising the steps of:
   (a) providing a feed stream comprising a metal-bearing material;
   (b) subjecting at least a portion of said feed stream to controlled, super-fine grinding to form an inlet stream, wherein said controlled, super-fine grinding comprises reducing the particle size of said feed stream to a P98 of less than about 25 microns;
   (c) leaching at least a portion of said inlet stream in the presence of oxygen at an elevated temperature and pressure to form a metal-bearing solution;
   (d) recovering at least one metal value from said metal-bearing solution.

2. The method of claim 1, wherein said step of providing a feed stream comprising a metal-bearing material comprises providing a feed stream comprising a copper sulfide ore or concentrate.

3. The method of claim 1, wherein said step of providing a feed stream comprising a metal-bearing material comprises providing a feed stream comprising chalcopyrite.

4. The method of claim 1, wherein said step of subjecting said feed stream to controlled, super-fine grinding comprises reducing the particle size of said feed stream to a P98 of from about 10 to about 23 microns.

5. The method of claim 1, wherein said step of subjecting said feed stream to controlled, super-fine grinding comprises reducing the particle size of said feed stream to a P98 of from about 13 to about 15 microns.

6. The method of claim 1, wherein said step of leaching said inlet stream comprises leaching said inlet stream at a temperature of from about 140° C. to about 180° C. and at a pressure of from about 100 psi to about 750 psi.

7. The method of claim 1, wherein said step of leaching said inlet stream comprises leaching said inlet stream at a temperature of from about 1500° C. to about 1750° C. and at a pressure of from about 100 psi to about 750 psi.

8. The meted of claim 1, wherein said step of leaching said inlet stream further comprises leaching said inlet stream in the presence of a surfactant.

9. The method of claim 1, wherein said step of leaching said inlet stream further comprises leaching said inlet stream in the presence of a surfactant selected from the group consisting of lignin derivatives, orthophenylene diamine, alkyl sulfonates, and mixtures thereof.

10. The method of claim 1, wherein said step of leaching said inlet stream further comprises leaching said inlet stream in the presence of calcium lignosulfonate.

11. The method of claim 1, wherein said step of leaching said inlet stream further comprises leaching said inlet stream in the presence of a surfactant in an amount of from about 2 to about 20 kilograms per tonne of concentrate in the inlet stream.

12. The method of claim 1 further comprising the step of combining at least a portion of said inlet stream with a liquid prior to step (c) to form an inlet stream having a solid-liquid ratio.

13. The method of claim 12, wherein said step of combining at least a portion of said inlet stream with a liquid comprises combining at least a portion of said inlet stream with at least one of process water, raffinate, pregnant leach solution, and lean electrolyte.

14. The method of claim 12, wherein said step of combining at least a portion of said inlet stream with a liquid comprises combining at least a portion of said inlet stream with a liquid to form an inlet stream having a solid-liquid ratio of from about 5 percent to about 50 percent.

15. The method of claim 12, wherein said step of combining at least a portion of said inlet stream with a liquid comprises combining at least a portion of said inlet stream with a liquid to form an inlet stream having a solid-liquid ratio of from about 10 percent to about 35 percent.

* * * * *